US011974773B2

(12) United States Patent
Scott et al.

(10) Patent No.: US 11,974,773 B2
(45) Date of Patent: May 7, 2024

(54) LATCHLESS OBTURATOR WITH INTERFERENCE FIT FEATURE

(71) Applicant: Cilag GmbH International, Zug (CH)

(72) Inventors: Gregory G. Scott, Cincinnati, OH (US); Jeffrey L. Savage, West Chester, OH (US)

(73) Assignee: Cilag GmbH International, Zug (CH)

( * ) Notice: Subject to any disclaimer, the term of this patent is extended or adjusted under 35 U.S.C. 154(b) by 182 days.

(21) Appl. No.: 17/213,434

(22) Filed: Mar. 26, 2021

(65) Prior Publication Data
US 2021/0338269 A1 Nov. 4, 2021

Related U.S. Application Data

(60) Provisional application No. 63/018,555, filed on May 1, 2020.

(51) Int. Cl.
A61B 17/34 (2006.01)
A61B 17/00 (2006.01)
A61M 13/00 (2006.01)

(52) U.S. Cl.
CPC ...... *A61B 17/3415* (2013.01); *A61B 17/3423* (2013.01); *A61B 2017/0023* (2013.01); *A61B 2017/3454* (2013.01); *A61M 13/003* (2013.01)

(58) Field of Classification Search
CPC ............ A61B 17/3415; A61B 17/3423; A61B 2017/3454; A61B 17/3462; A61B 17/34;
(Continued)

(56) References Cited

U.S. PATENT DOCUMENTS 4,699,616 A 10/1987 Nowak et al.
5,147,316 A 9/1992 Castillenti
(Continued)

FOREIGN PATENT DOCUMENTS

AU 702882 B2 3/1993
CN 106344126 B 2/2019
(Continued)

OTHER PUBLICATIONS

International Search Report and Written Opinion dated Jul. 22, 2021, for International Application No. PCT/EP2021/061421, 15 pages.
(Continued)

*Primary Examiner* — Lauren P Farrar
*Assistant Examiner* — Kathleen Paige Farrell
(74) *Attorney, Agent, or Firm* — Frost Brown Todd LLP

(57) ABSTRACT

A surgical access device includes a cannula assembly and an obturator. The obturator is configured to removably couple with the cannula assembly along a central axis of the cannula assembly to facility inversion of the surgical access device through a body wall of the patient. The obturator includes an elongated shaft extending along a longitudinal axis, a tapered distal tip located at a distal portion of the elongated shaft, and an obturator head located at a proximal portion of the elongated shaft. The obturator head includes an interference fit feature capable of inhibiting proximal movement between the obturator and the cannula assembly via a frictional force against a surface of the cannula assembly.

13 Claims, 14 Drawing Sheets

(58) Field of Classification Search
CPC ............ A61B 17/3421; A61B 17/3417; A61B 2090/034; A61B 2090/035; A61B 90/03; A61B 2017/00477; A61B 2017/347; A61M 13/003
See application file for complete search history.

(56) References Cited

U.S. PATENT DOCUMENTS

| | | | |
|---|---|---|---|
| 5,215,531 A | 6/1993 | Maxson et al. | |
| 5,256,147 A | 10/1993 | Vidal et al. | |
| 5,263,939 A | 11/1993 | Wortrich | |
| 5,267,970 A * | 12/1993 | Chin | A61M 25/02 604/174 |
| 5,364,372 A | 11/1994 | Danks et al. | |
| 5,792,135 A | 8/1998 | Madhani et al. | |
| 5,800,451 A | 9/1998 | Buess et al. | |
| 5,817,061 A | 10/1998 | Goodwin et al. | |
| 5,833,666 A | 11/1998 | Davis et al. | |
| 6,638,265 B1 | 10/2003 | Ternamian | |
| 7,981,092 B2 | 7/2011 | Duke | |
| 8,226,553 B2 | 7/2012 | Shelton, IV et al. | |
| 8,251,900 B2 | 8/2012 | Ortiz et al. | |
| 8,479,969 B2 | 7/2013 | Shelton, IV | |
| 8,568,362 B2 | 10/2013 | Moreno, Jr. et al. | |
| 8,573,465 B2 | 11/2013 | Shelton, IV | |
| 8,579,807 B2 | 11/2013 | Moreno, Jr. et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 10,058,336 B2 * | 8/2018 | Truckai et al. | A61B 17/1671 |
| 10,327,809 B2 | 6/2019 | Buyda et al. | |
| 10,792,069 B2 | 10/2020 | Hall et al. | |
| 10,820,924 B2 | 11/2020 | Hall et al. | |
| 2009/0182282 A1 | 7/2009 | Okihisa et al. | |
| 2009/0221876 A1 * | 9/2009 | Cobb | A61B 17/3421 604/164.11 |
| 2009/0234292 A1 * | 9/2009 | Di Nardo | A61B 17/3462 604/167.01 |
| 2010/0010449 A1 | 1/2010 | Leibowitz et al. | |
| 2013/0060084 A1 | 3/2013 | Fouts et al. | |
| 2014/0066953 A1 | 3/2014 | Keating et al. | |
| 2016/0015423 A1 | 1/2016 | Ravikumar et al. | |
| 2018/0168686 A1 * | 6/2018 | Jin et al. | A61B 5/361 |
| 2018/0199959 A1 | 7/2018 | Lee | |
| 2018/0206883 A1 | 7/2018 | McIntyre et al. | |
| 2019/0000496 A1 | 1/2019 | Shelton, IV et al. | |
| 2019/0000505 A1 * | 1/2019 | Parihar | A61B 17/3421 |
| 2019/0380742 A1 | 12/2019 | Hall et al. | |
| 2021/0085355 A1 * | 3/2021 | Riley, III | A61B 10/02 |
| 2021/0338272 A1 | 11/2021 | Muthuchidambaram et al. | |
| 2021/0338273 A1 | 11/2021 | Vijayachandran et al. | |
| 2021/0338274 A1 | 11/2021 | Scott et al. | |
| 2021/0338275 A1 | 11/2021 | Vijayachandran | |
| 2021/0338276 A1 | 11/2021 | Scott | |
| 2021/0338278 A1 | 11/2021 | Scott et al. | |
| 2021/0338281 A1 | 11/2021 | Mozloom, Jr. et al. | |
| 2021/0338282 A1 | 11/2021 | Vijayachandran | |
| 2021/0338283 A1 | 11/2021 | McLain | |
| 2021/0338371 A1 | 11/2021 | Harris et al. | |

FOREIGN PATENT DOCUMENTS

| | | |
|---|---|---|
| DE | 202007001745 U1 | 4/2007 |
| EP | 2174602 A1 | 4/2010 |
| WO | WO 1999/052457 A1 | 10/1999 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.

International Search Report and Written Opinion dated Jul. 16, 2021, for International Application No. PCT/EP2021/061442, 13 pages.

International Search Report and Written Opinion dated Jul. 8, 2021, for International Application No. PCT/EP2021/061447, 15 pages.

International Search Report and Written Opinion dated Jul. 27, 2021, for International Application No. PCT/EP2021/061456, 14 pages.

International Search Report and Written Opinion dated Jul. 13, 2021, for International Application No. PCT/EP2021/061459, 16 pages.

International Search Report and Written Opinion dated Jul. 20, 2021, for International Application No. PCT/EP2021/061466, 17 pages.

International Search Report and Written Opinion dated Jul. 15, 2021, for International Application No. PCT/EP2021/061468, 16 pages.

* cited by examiner

LATCHLESS OBTURATOR WITH INTERFERENCE FIT FEATURE

PRIORITY

This application claims priority to U.S. Provisional Pat. App. No. 63/018,555, entitled "Latchless Obturator with Interference Fit Feature," filed on May 1, 2020.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Pre-defined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019, issued as U.S. Pat. No. 11,389,192 on Jul. 19, 2022. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
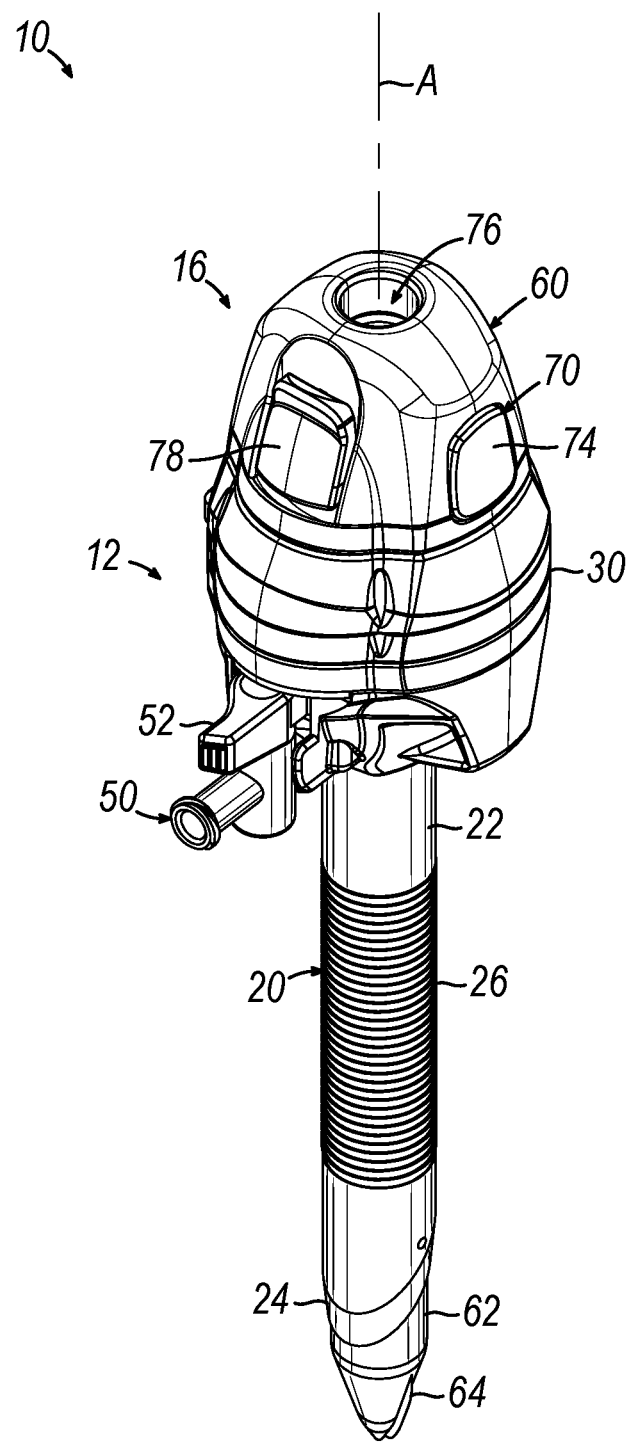
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other clinician, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
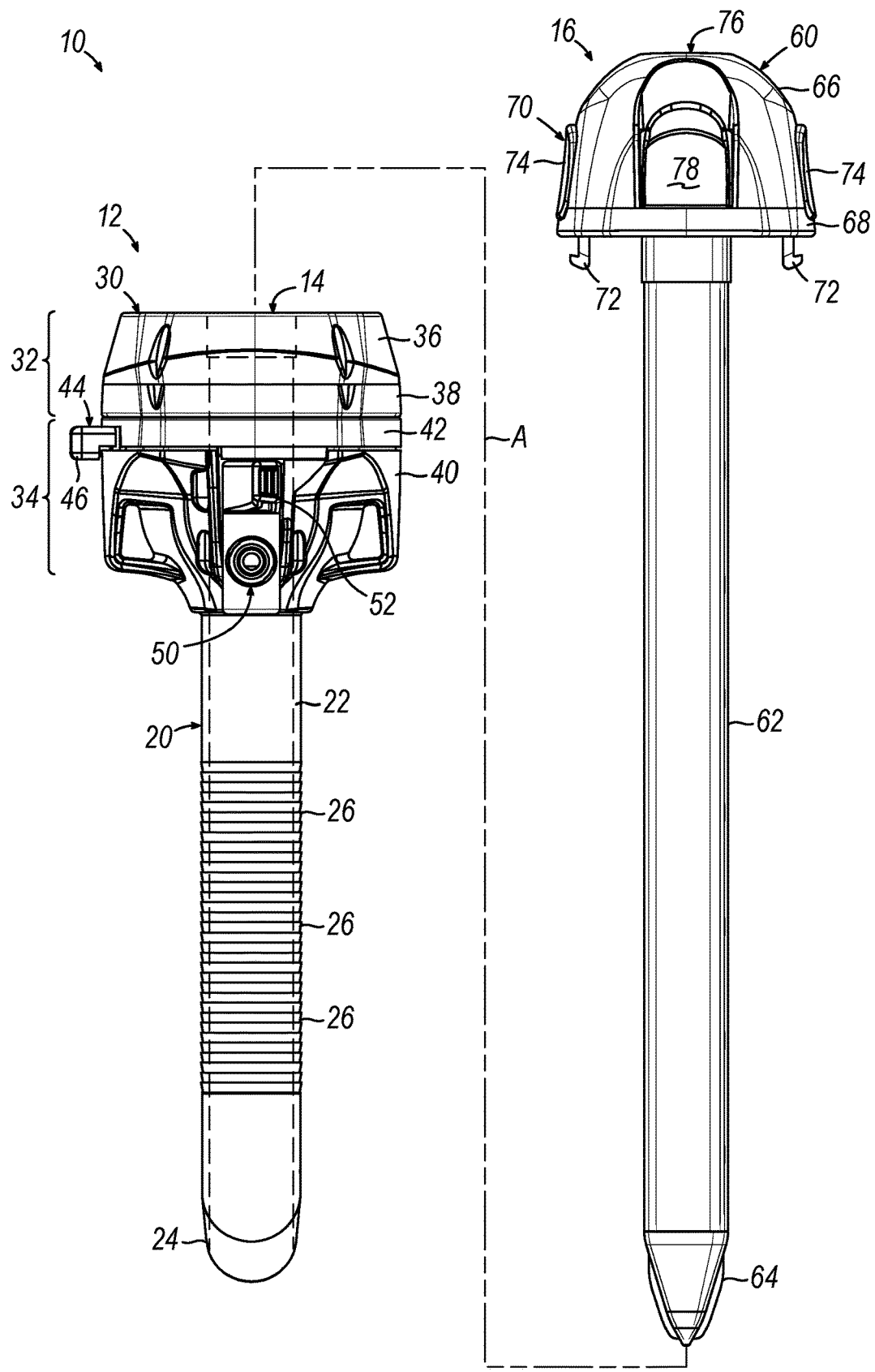
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (35) (See FIG. 7A) formed in a top surface of seal housing head (36) to couple obturator (16) with cannula assembly (12). Latch buttons (74) are actuatable to release latch arms (72) from the slots (35) and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
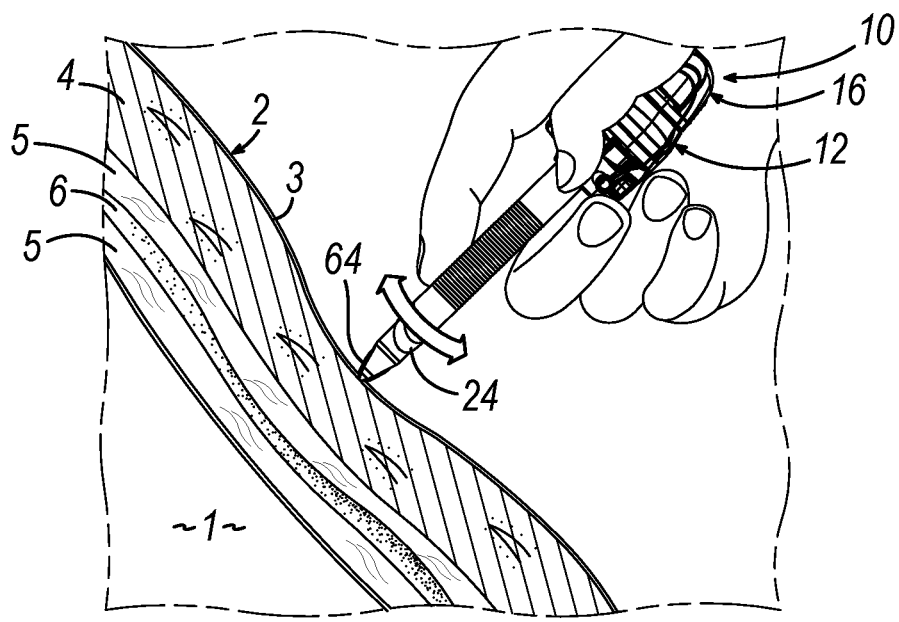
FIG. 3A depicts a side sectional view of the trocar of FIG. 1 being manipulated by a clinician through tissue layers of an abdominal wall.
Figure 3B:
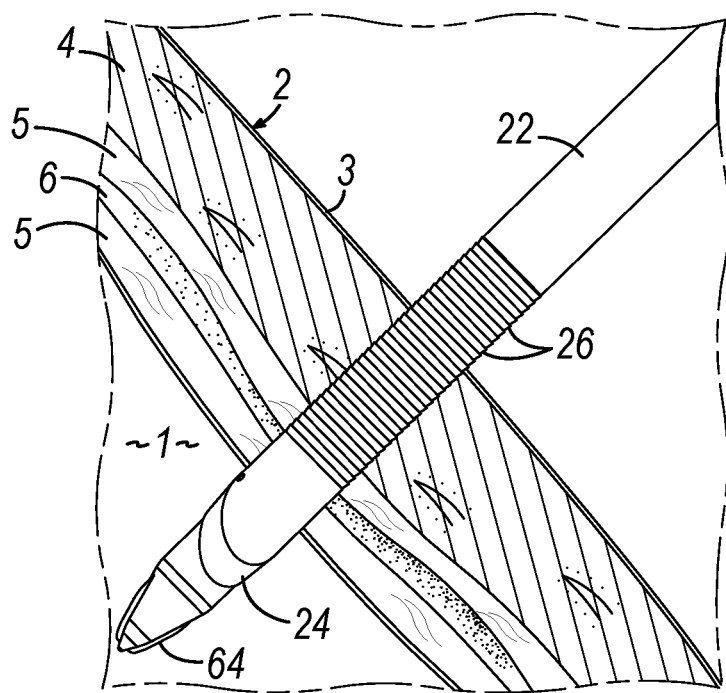
FIG. 3B depicts an enlarged side sectional view of the trocar of FIG. 1, showing a distal end of the trocar received within the abdominal cavity of FIG. 3A.
Figure 3C:
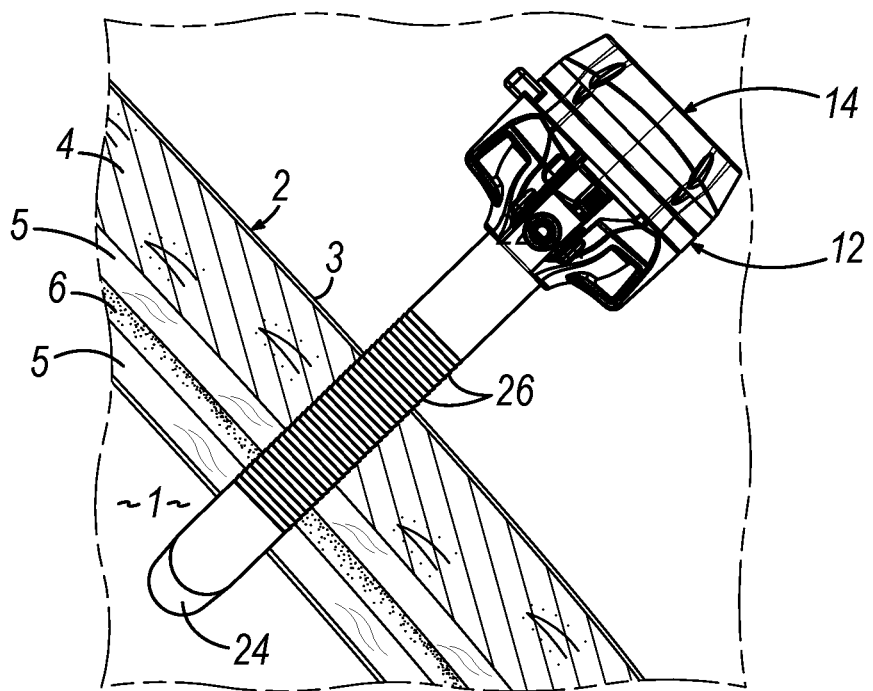
FIG. 3C depicts a side sectional view of the cannula assembly of FIG. 1, showing the cannula assembly remaining positioned within the abdominal wall of FIG. 3A following detachment and removal of the obturator.
Figure 3D:
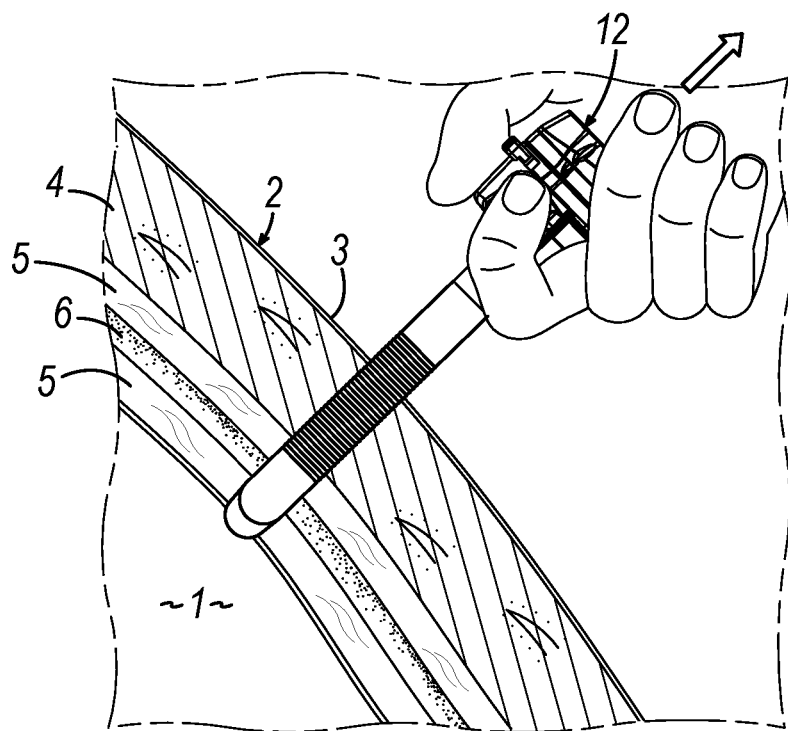
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
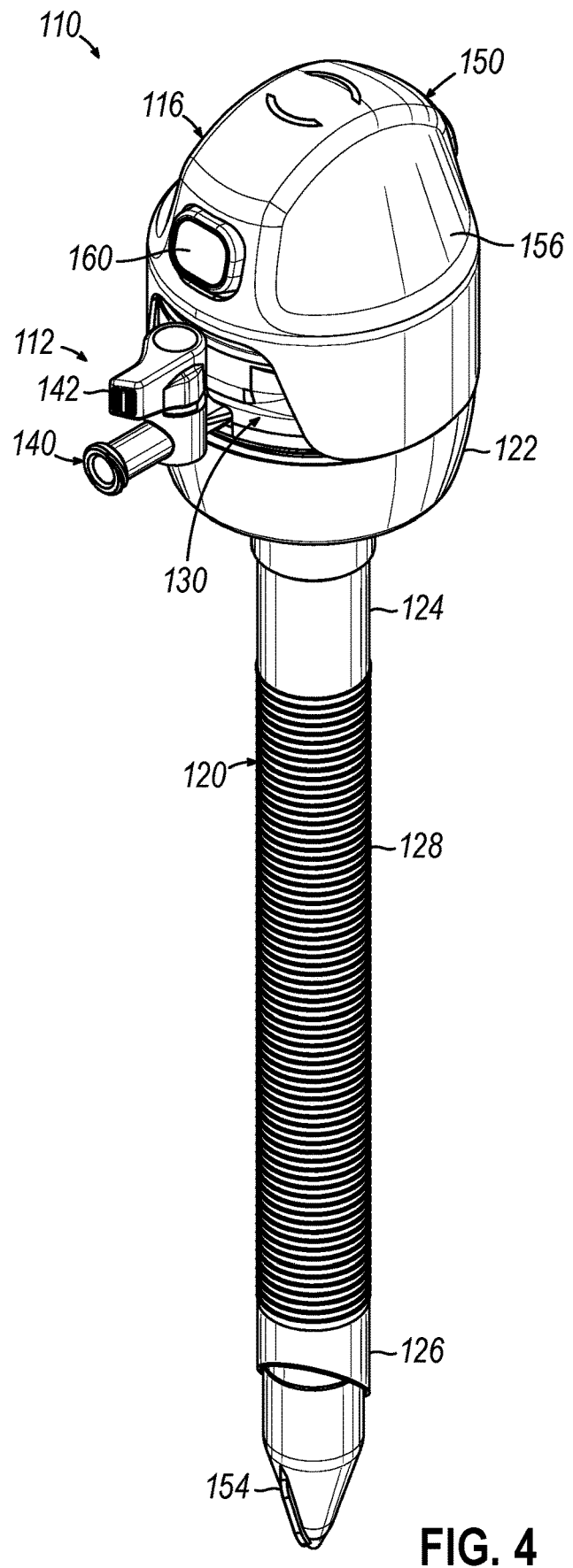
FIG. 4 depicts a perspective view of another exemplary trocar having a cannula assembly and an obturator shown in an assembled state.
Figure 5:
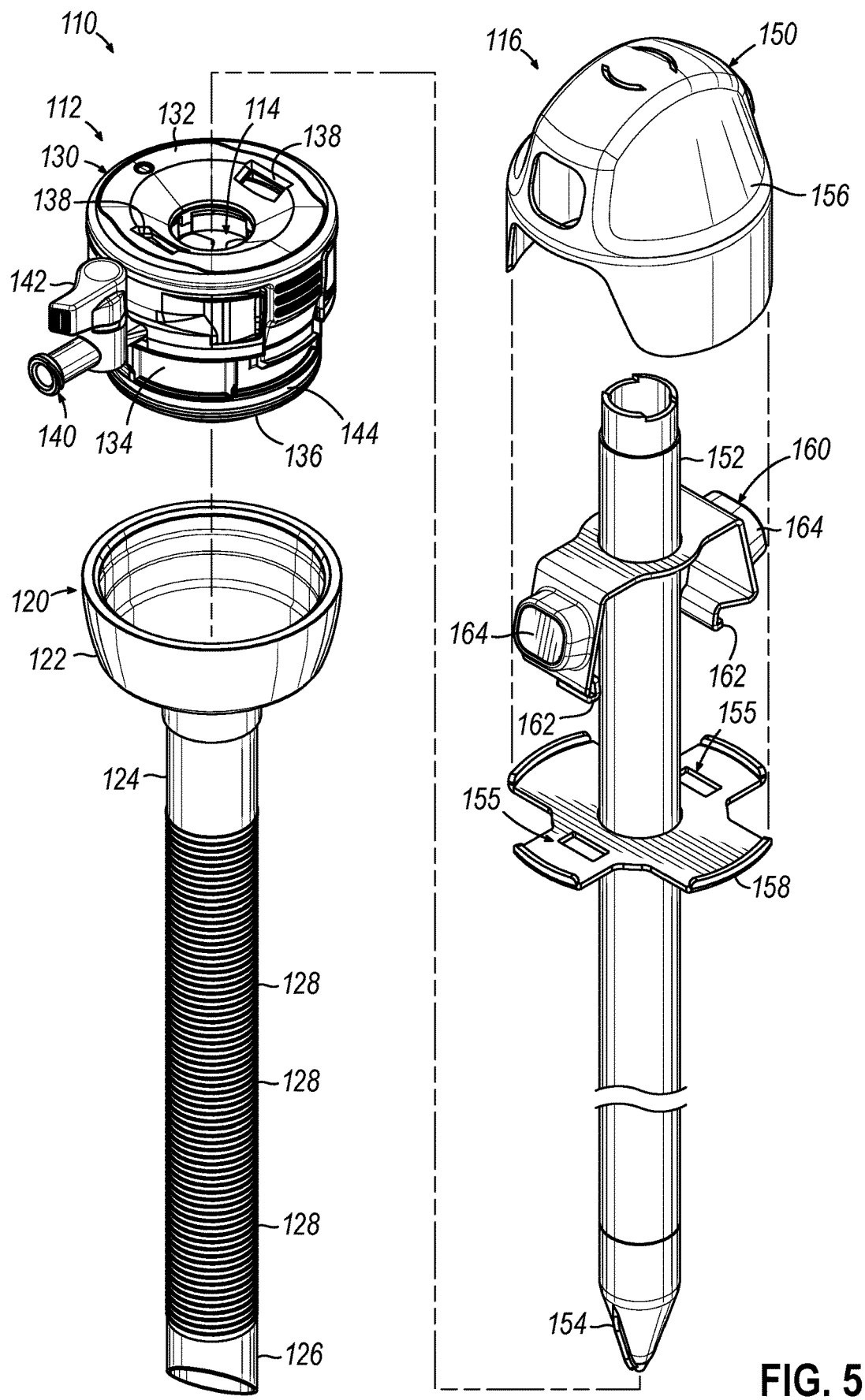
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, issued as U.S. Pat. No. 10,792,069 on Oct. 6, 2020, the disclosure of which is incorporated by reference herein; and/or U.S. Pat. Pub. No. 2019/0380742, entitled "Asymmetric Shaft Seal," published Dec. 19, 2019, issued as U.S. Pat. No. 10,820,924 on Nov. 3, 2020, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Latchless Obturator

As mentioned above, each actuatable latch member (70, 160) includes a respective pair of latch arms (72, 162) and a corresponding pair of latch buttons (74, 164). Respective latch arms (72, 162) are configured to be captured within respective slots (35, 138) of an assembled cannula assembly (12, 112) to couple obturator (16, 116) with cannula assembly (12, 112). Additionally, latch buttons (74, 164) are actuatable to release latch arms (72, 162) from the slots (35, 138) and thereby permit separation of obturator (16, 116) from cannula assembly (12, 112).

Therefore, latch member (70, 160) may be used to couple obturator (16, 116) with cannula assembly (12, 112) while trocar (10, 110) is used to access cavity (1) in accordance with the description herein. Once cannula (20, 120) has reached a desired depth of insertion into cavity (1), the clinician may decouple obturator (16, 116) from cannula assembly (12, 112) by depressing latch buttons (74, 164), and then withdrawing obturator (16, 116) proximally from cannula assembly (12, 112), as shown in FIG. 3C. The clinician may depress latch buttons (74, 164) with one hand via a pinching motion with the thumb and another finger, such as the index finger. In other words, in order for the clinician to decouple obturator (16, 116) from cannula assembly (12, 112), the clinician must (A) depress latch buttons (74, 164) to deflect latch arms (72, 162) out of suitable engagement with cannula assembly (12, 112), and (B) pull obturator (16, 116) proximally relative to cannula assembly (12, 112) while latch buttons (74, 164) are suitably depressed in order to decouple obturator (16, 116) from cannula assembly (12, 112).

In order to actuate latch arms (72, 162) via depression of latch buttons (74, 164) in accordance with the description herein, latch arms (72, 162) may require a suitable geometry to promote relatively easy actuation of latch arms (72, 162) via depression of latch buttons (74, 164). A suitable geometry of latch arms (72, 162) may include a leaf-spring geometry having an aspect ratio that includes a relatively long length compared to thickness.

In instances where obturator (116) is configured to be sterilized and reused for multiple surgical procedures, the long and thin geometry of latch arms (162), for purposes of coupling and decoupling obturator (116) with cannula assembly (112), may leave latch arms (162) vulnerable to damage during the sterilization processes. Such damage may prevent actuatable latch member (160) from functioning in accordance with the description herein. For instance, a user who is cleaning and sterilizing a used obturator (116) may accidentally bend latch arms (162) relative to latch buttons (164) to such a degree that latch arms (162) are permanently damaged. Permanent damage of latch arms (162) may prevent latch buttons (164) from suitably decoupling latch arms (162) with cannula assembly (112) in accordance with the description herein.

As best seen in FIG. 5, obturator (116) may include base plate (158) defining reinforcing slots (155) configured to help prevent unintentional damage to latch arms (162). Reinforcing slots (155) are dimensioned to house latch arms (162). In particular, reinforcing slots (155) may allow latch arms (162) to suitably deflect in response to depression of latch buttons (164) so latch arms (162) may couple and decouple obturator (116) with cannula assembly (112) in accordance with the description here. Additionally, reinforcing slots (155) may reinforce latch arms (162) to help prevent accidental damage during exemplary use and sterilization. For instance, reinforcing slots (155) may abut against portions of respective latch arms (162) in incidences of accidental contact, thereby reinforcing latch arms (162) help prevent accidental damage to latch arms (162).

However, the presence of base plate (158) and reinforcing slots (155) may create various other issues related to proper sterilization of obturator (116). For example, the area between base plate (158) and domed upper body (156) may become difficult to access for suitable sterilization. It may be difficult for a fluid to suitably enter or exit the interior area defined by base plate (158) and domed upper body (156) in order to suitably sterilize all surfaces of obturator (116) located within the interior area. As another example, external matter may become trapped in the interior area defined by base plate (158) and domed upper body (156) without suitable access to remove such matter.

Therefore, it may be desirable to have an obturator configured (A) to couple and decouple via a coupling assembly, and (B) to be suitably sterilized and reused for multiple surgical procedures while preventing unintentional damage to the coupling assembly.

Figure 6:
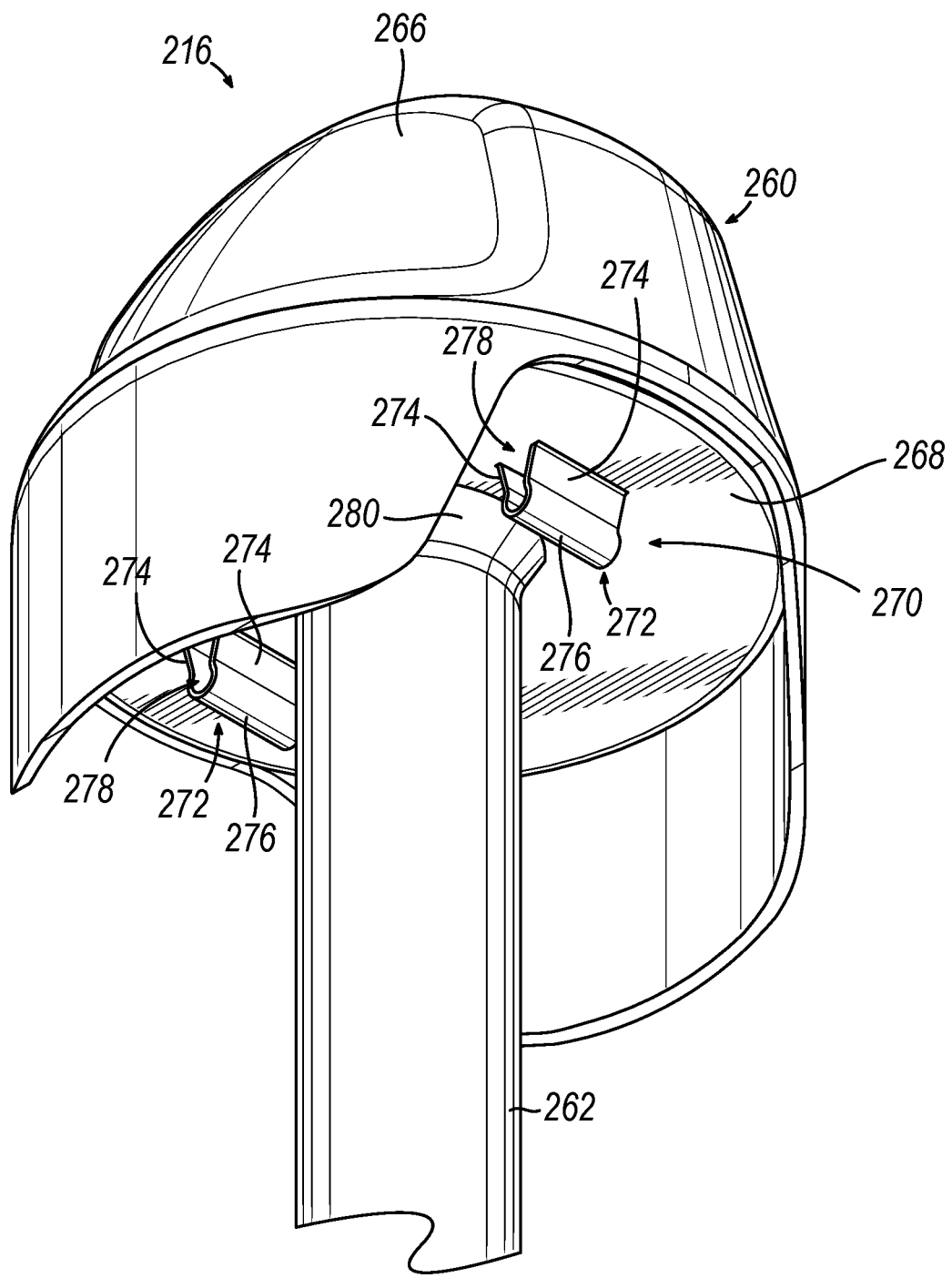
FIG. 6 depicts an enlarged perspective view of a proximal end of another exemplary obturator.

FIG. 6 shows a proximal end of an obturator (216) that may be readily incorporated into trocar (10, 110) in replacement of obturator (16, 116) described above. Obturator (216) may be substantially similar to obturator (116) mentioned above, with differences described below. Therefore, obturator (216) may be suitably constructed of a robust material, such as surgical steel, such that obturator (216) may be sterilized and reused for multiple surgical procedures. Obturator (216) includes a proximal head (260), an elongate cylindrical shaft (262) extending distally from proximal head (260), and a tapered distal tip (264) (See FIGS. 8A-8B).

Elongate cylindrical shaft (262) and tapered distal tip (264) may be substantially similar to elongate cylindrical shaft (62, 152) and tapered distal tip (64, 154) described above. Therefore, cylindrical shaft (262) is configured to be received within working channel (14, 114) of cannula assembly (12, 112) such that obturator tip (264) extends through and distally of cannula tip (24, 126).

Obturator head (260) includes a domed upper body (266), a base plate (268), and an interference fit coupling assembly (270). As will be described in greater detail below, interference fit coupling assembly (270) of obturator (216) is configured to suitably couple obturator (216) with cannula assembly (12) in order to form a trocar (210). As will also be described in greater detail below, interference fit coupling assembly (270) may be configured to (A) improve the robustness and/or durability of obturator (216) compared to actuatable latch member (160) of obturator (116), and (B) improve the cleanability of obturator (216) compared to obturator (116) by sealing off difficult to access areas for sterilization purposes.

In the current example, interference fit coupling assembly (270) includes a pair of spring clips (272) and a tapered shaft surface (280). Tapered shaft surface (280) extends from elongate shaft (262) toward base plate (268) such that the area of tapered shaft surface (280) closer to base plate (268) is wider than the area of tapered shaft surface (280) extending distally from base plate (268). As will be described in greater detail below, tapered shaft surface (280) is dimensioned to abut against a slanted upper surface (37) of seal housing (30) defining working channel (14) in order to promote the coupling of obturator (216) with cannula assembly (12) via friction fitting.

Each spring clip (272) includes a pair of legs (274) and a central portion (276). A proximal end of each leg (274) extends distally from a distal surface of base plate (268) in a tapered fashion such that the distal end of each leg (274) is closer to each other compared to the proximal end of each leg (274). The distal end of each leg (274) terminates into central portion (276) such that central portion (276) connects distal ends of each leg (274). Central portion (276) expands from the distal end of each leg (274) so the distance between the distal end of each leg (274) is closer than the distance between adjacent locations of central portion (276), as viewed from the perspective shown in FIGS. 7A-7B.

Legs (274), central portion (276), and the distal surface of base plate (268) define a pathway (278) that is open on both ends of spring clip (272). Spring clips (272) are formed of a sufficiently resilient material such that legs (274) and opposite sides of central portion (276) may flex inwardly relative to each other in response to an external compressive force, thereby altering the cross-sectional size of pathway (278). Additionally, spring clips (272) are formed of a sufficiently resilient material such that legs (274) and opposite sides of central portion (276) may expand back to their original shape once the external compressive force is removed, thereby allowing pathway (278) to return to its original cross-sectional size. As will be described in greater detail below, spring clips (272) are dimensioned to fit within respective slots (35) of seal housing (30) in order to promote the coupling of obturator (216) with cannula assembly (12) via friction fitting.

Figure 7A:
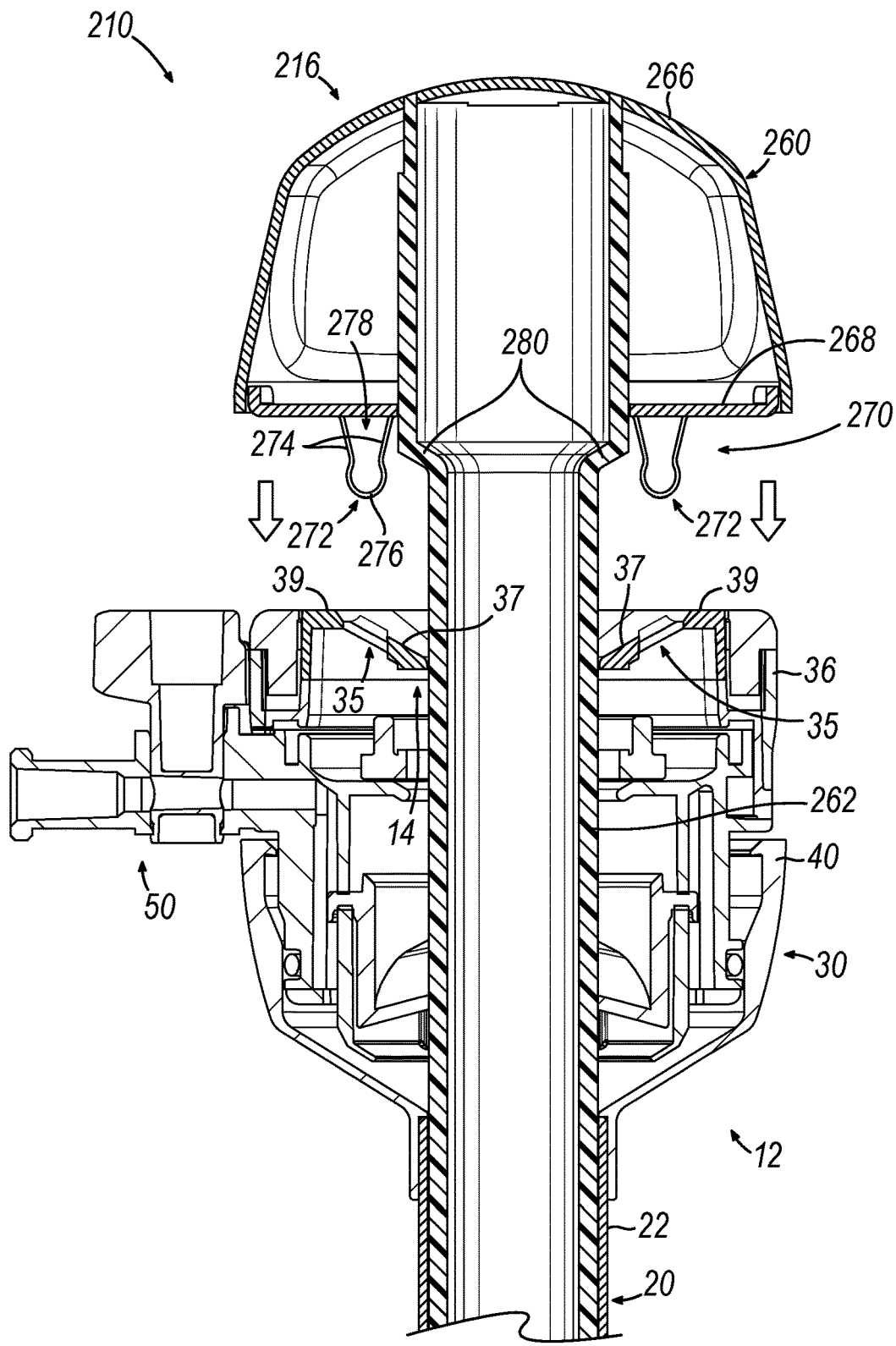
FIG. 7A depicts an enlarged cross-sectional view of a proximal end of another exemplary trocar including the obturator of FIG. 6 and the cannula assembly of FIG. 1 in a partially disassembled state.
Figure 7B:
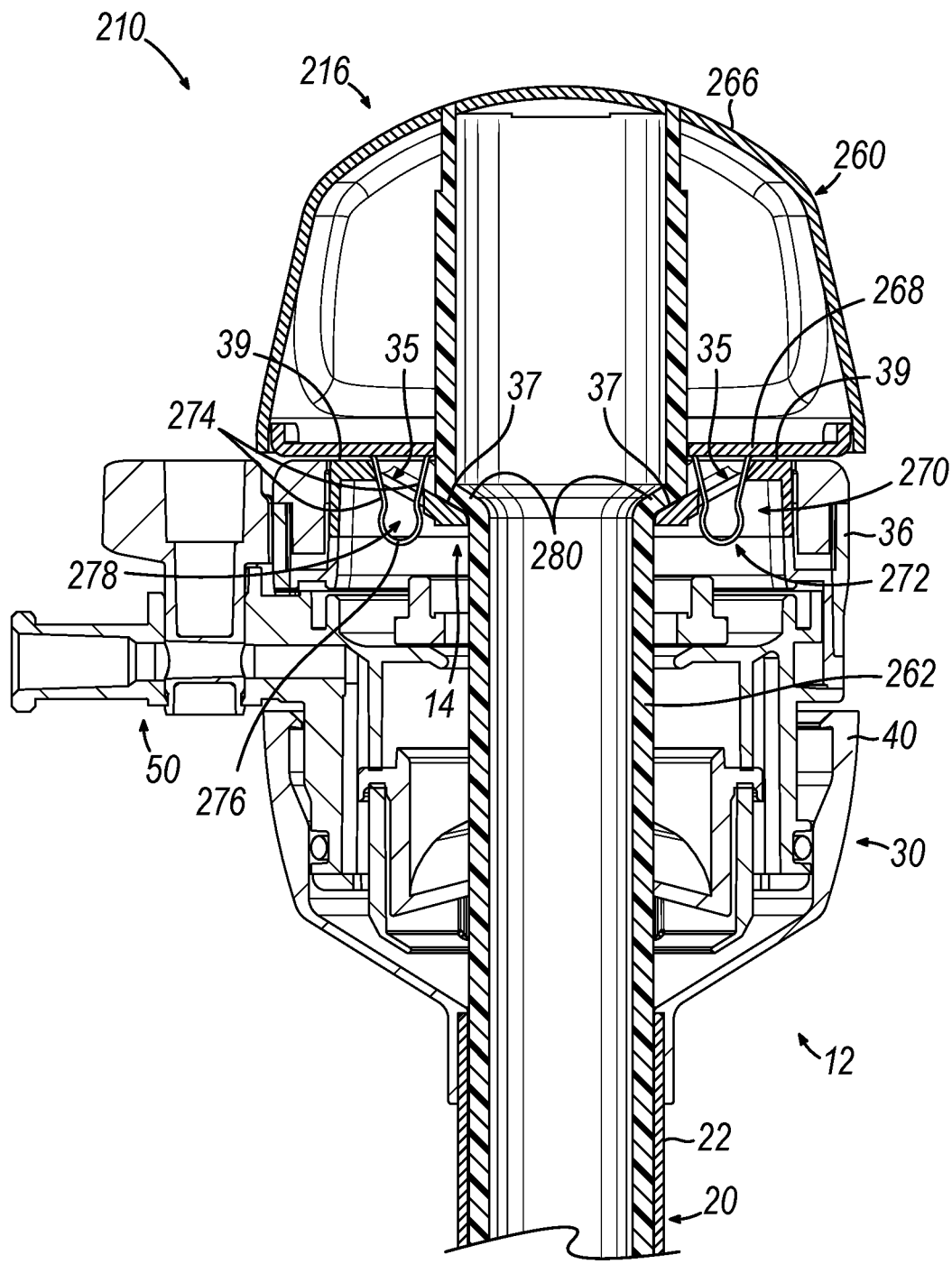
FIG. 7B depicts an enlarged cross-sectional view of the proximal end of the trocar of FIG. 7A, where the obturator of FIG. 6 and the cannula assembly of FIG. 1 are in an assembled state.
Figure 8A:
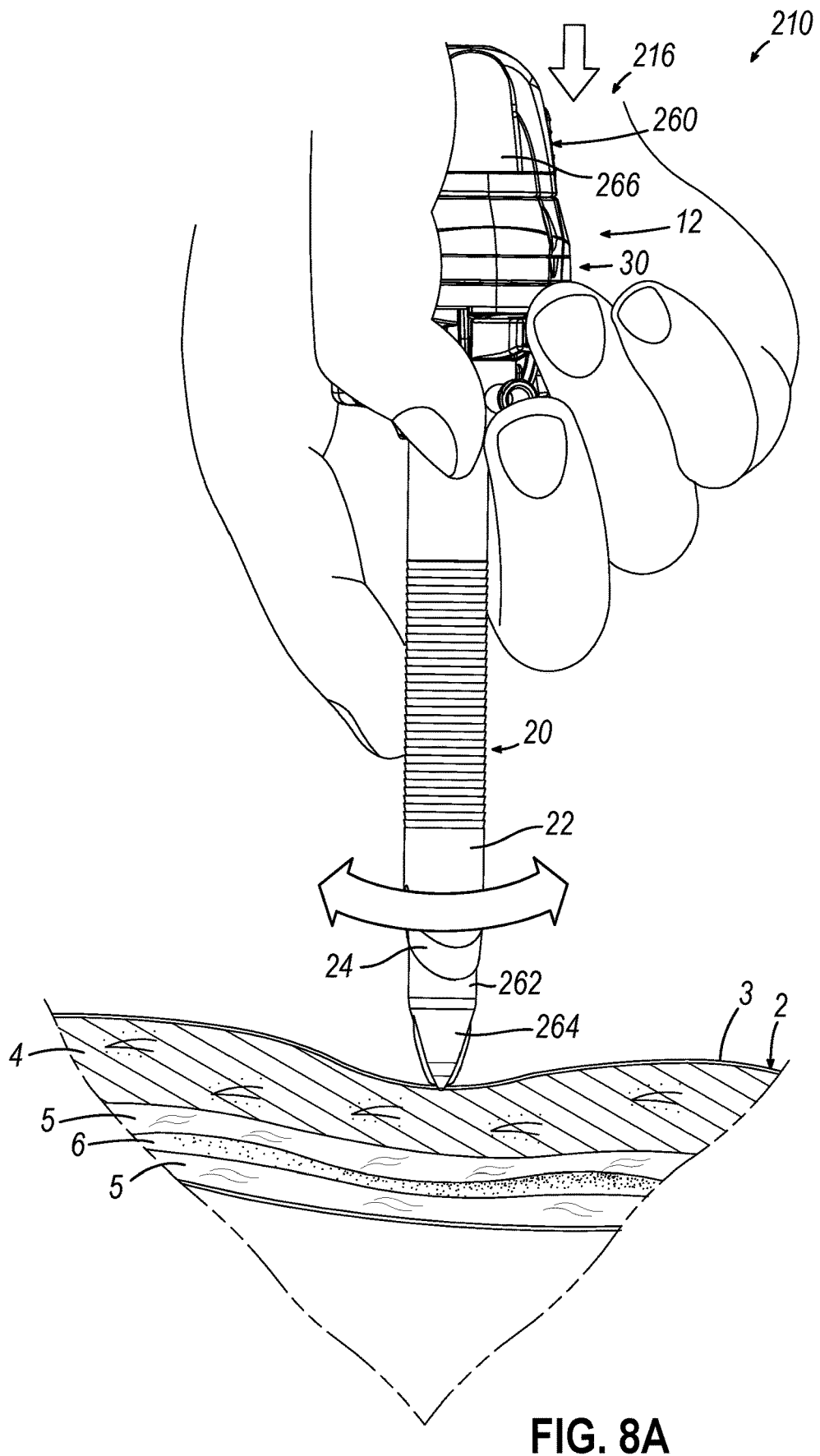
FIG. 8A depicts a side sectional view of the trocar of FIG. 1 being manipulated by a clinician through tissue layers of an abdominal wall.
Figure 8B:
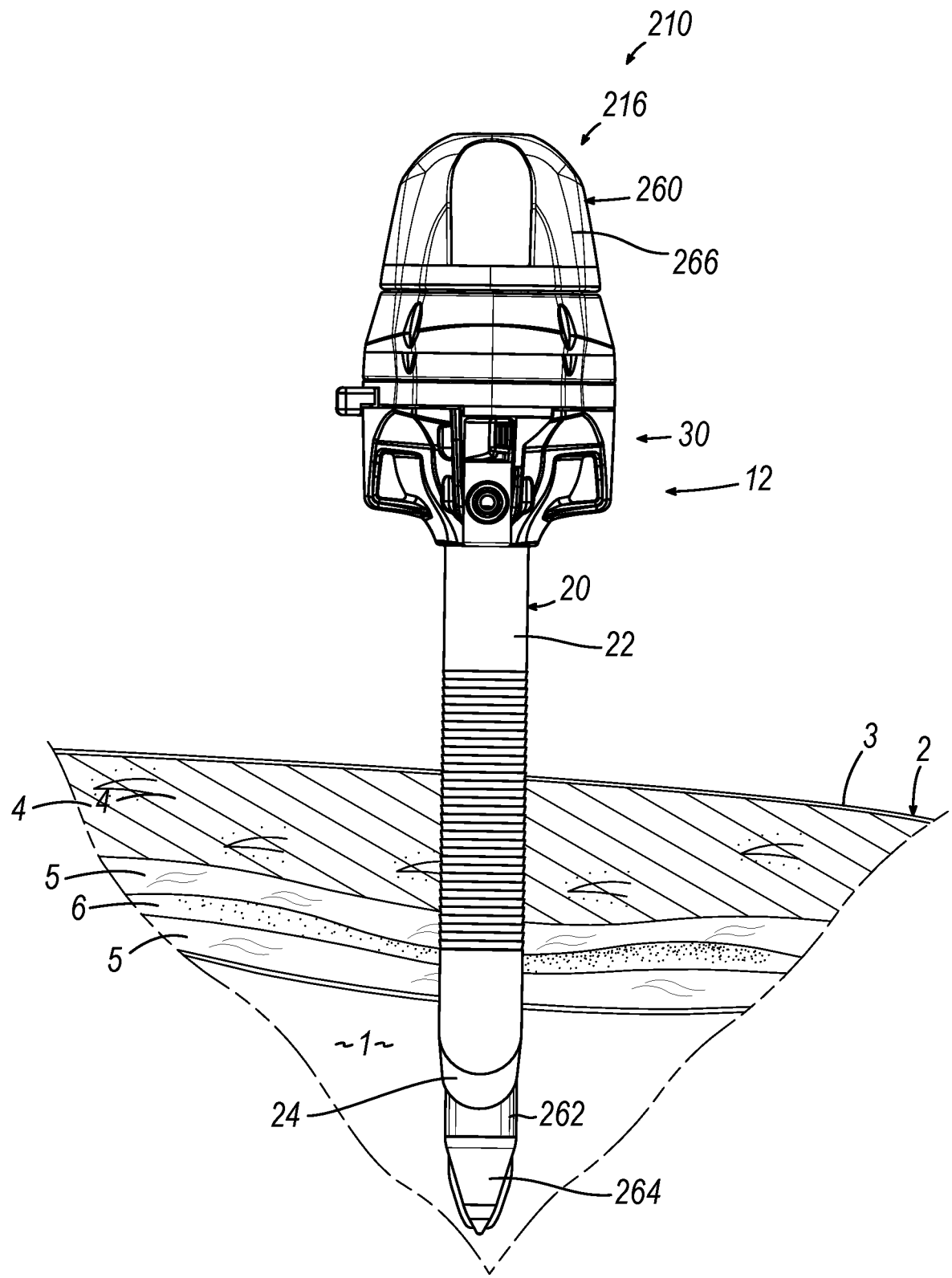
FIG. 8B depicts a side sectional view of the trocar of FIG. 7A, showing a distal end of the trocar received within an abdominal cavity.
Figure 8C:
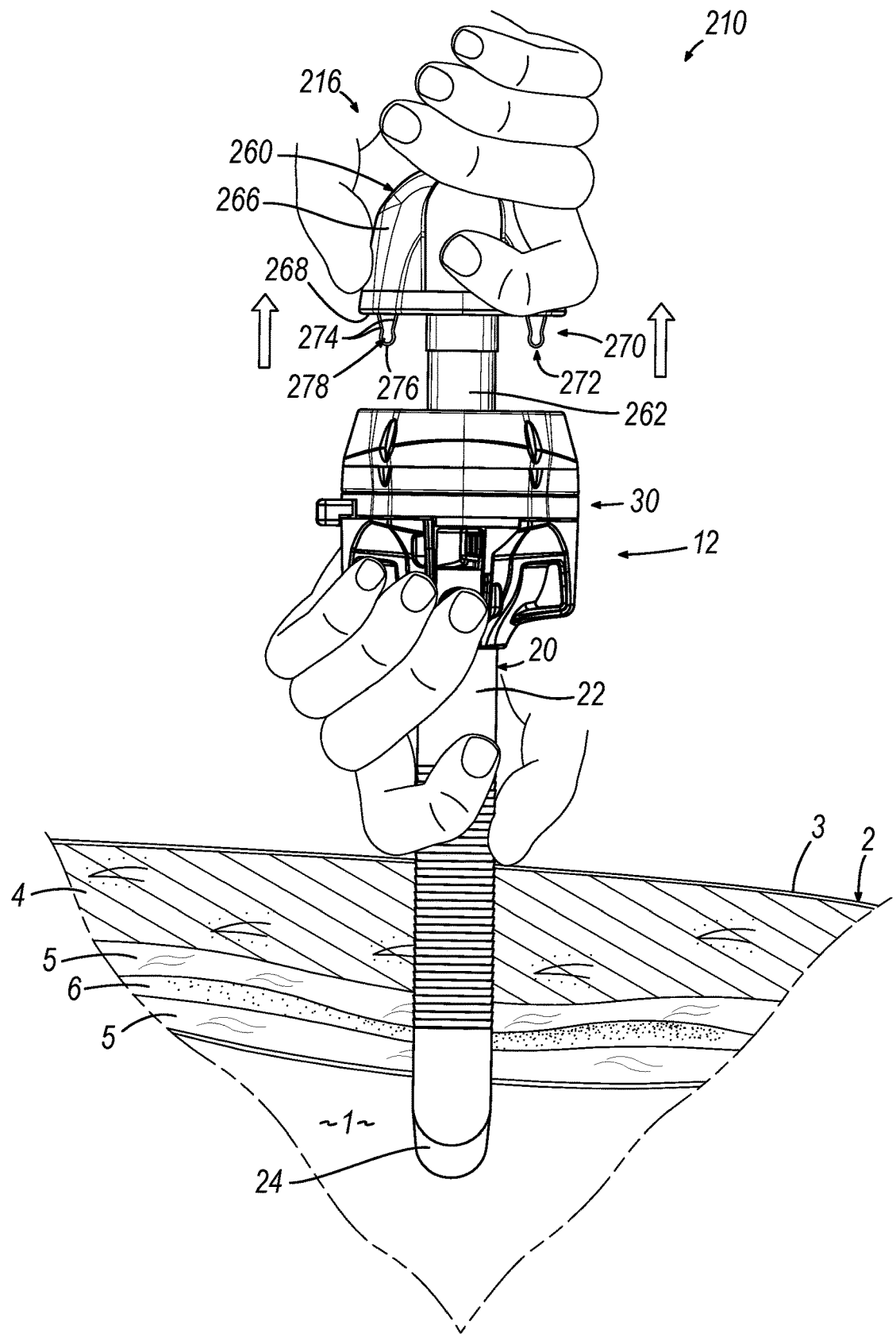
FIG. 8C depicts a side sectional view of the trocar of FIG. 7A, showing the cannula assembly remaining positioned within the abdominal wall of FIG. 8A while the obturator is proximally retracted from the cannula assembly.

FIGS. 7A-8C show an exemplary use of obturator (216) and cannula assembly (12) as a trocar (210) to access the abdominal cavity of a patent (1) through the patient abdominal wall (2). In particular, FIGS. 7A-7B show an exemplary coupling of obturator (216) with cannula assembly (12), while FIGS. 8A-8C show an exemplary use of the assembled trocar (210) and eventual decoupling of obturator (216) from cannula assembly (12).

FIG. 7A shows elongate shaft (262) inserted within working channel (14) of cannula assembly (12) such that tapered shaft surface (280) is proximal relative to slanted upper surface (37) of seal housing (30). Additionally, spring clips (272) are proximal relative to slots (35), but suitably aligned with slots (35) for coupling purposes. At the moment shown in FIG. 7A, obturator (216) is not suitably coupled with cannula assembly (12).

Next, as shown in FIG. 7B, the clinician may further actuate obturator head (260) and cannula assembly (12) toward each other such that tapered shaft surface (280) engages with slanted upper surface (37) of seal housing (30), and such that spring clips (272) are driven into their respective slots (35). Engagement between tapered shaft surface (280) and slanted surface (37), as well as retention of spring clips (272) within respective slots (35), may help promote an interference fit coupling between obturator (216) and cannula assembly (12) in order to form trocar (210).

In some instances, engagement between tapered shaft surface (280) and slanted surface (37) may cause deformation of tapered shaft surface (280) and/or slanted surface (37). Additionally, in some instances, engagement between spring clips (272) and the portion of seal housing (30) defining slots (35) may cause deformation of spring clips (272) and/or the portion of seal housing (30) defining slots (35). Such deformation may further promote the interference fit coupling between obturator (216) and cannular assembly (12).

Tapered shaft surface (280) and slanted upper surface (37) of seal housing (30) may have complementary surfaces, such that when the clinician actuates obturator head (260) and cannula assembly (12) toward each other, engagement between tapered shaft surface (280) and slanted upper surface (37) promotes a frictional braking force that may prevent obturator head (260) from actuating any further relative to cannula assembly (12) in the distal direction. The frictional braking force generated between surfaces (37, 280) by actuating of obturator head (260) and cannula assembly (12) toward each other may create a suitable interference fit coupling between surfaces (37, 280) strong enough to suitably prevent accidental decoupling of obturator (216) and cannula assembly (12) during exemplary use in accordance with the description herein. In other words, the frictional engagement between surfaces (37, 280) may help suitably prevent obturator (216) from proximally decoupling with cannula assembly (12). For instance, the friction engagement between surfaces (37, 280) may be strong enough to keep trocar (210) assembled while the clinician grabs trocar (210) solely by obturator head (260).

It should be understood that slanted upper surface (37) and tapered shaft surface (280) engage each other along a plane such that a the frictional resistance to motion between surfaces (37, 280) has at least a partial component that extends along the mating path between obturator (216) and cannula assembly (12). The partial component of frictional resistance to motion between surfaces (27, 280) may be sufficiently strong enough to prevent obturator (216) from proximally decoupling with cannula assembly (12).

Slots (35) of seal housing (30) are defined by an outer lip (39) and slanted upper surface (37). Slots (35) are dimensioned narrower compared to the widest portion of spring clips (272). Therefore, when the clinician actuates obturator head (26) and cannula assembly (12) toward each other, spring clips (272) make contact with the portions of seal housing (30) defining slots (35). Such contact may drive legs (274) and opposite sides of central portion (276) to flex inwardly relative to each other, thereby altering the cross-sectional size of pathway (278). The contact between the portion of seal housing (30) defining slots (35) and spring clips (272) that causes spring clip (237) to flex inwards may generate a sufficient frictional braking force strong enough to suitably prevent accidental decoupling of obturator (216) and cannula assembly (12) during exemplary use in accordance with the description herein. For instance, the friction engagement between slots (35) and spring clips (272) may be strong enough to keep trocar (210) assembled while the clinician grabs trocar (210) solely by obturator head (260).

It should be understood that spring clips (272) and slots (35) engage each other along a plane such that the frictional resistance to motion between surfaces of spring clips (272) and slots (35) has at least a partial component that extends along the mating path between obturator (216) and cannula assembly (12). The partial component of frictional resistance to motion between surfaces of spring clips (272) and slots (35) may be sufficiently strong enough to prevent obturator (216) from proximally decoupling with cannula assembly (12).

Additionally, central portion (276) may initially deform while being inserted into slots (35), and then extend distally within slots (35) far enough to no longer make contact with portions of seal housing (30) defining slots (35). In such an instance, the resilient nature of spring clips (272) may allow central portion (276) to return toward its initial shape such that the widest portion of central portion (276) is wider than slots (35). Therefore, contact between central portion (276) and the portion of seal housing (30) defining slots (35) may further prevent accidental decoupling of obturator (216) with cannula assembly (12) during exemplary use.

In some instances, spring clips (272) may not be resilient at all. In such instances, spring clips (272) may be more like downwardly extending pins that create a frictional force with slots (35) in a similar manner as tapered shaft surface (280) and slanted upper surface (37) described above.

With obturator (216) suitably coupled with cannula assembly (12) to form trocar (210), the clinician may proceed to use trocar (210) to access the abdominal cavity of a patent (1) through the patient abdominal wall (2). As best shown in FIG. 8A, with obturator (216) received within cannula assembly (12) and connected to seal housing (30), a clinician manipulates trocar (210) via obturator head (260) and seal housing (30) to urge obturator tip (264) against skin (3) and inward toward abdominal cavity (1) while rotating trocar (210) back and forth. It should be understood that as the clinician manipulates trocar (210) inward toward abdominal cavity (1), springs clips (272) and tapered shaft surface (280) may be further actuated into engagement cannula assembly (12). Therefore, while obturator tip (264) is urged into abdominal cavity (1), the chances of the clinician overcoming the friction fitting between obturator (216) and cannula assembly (12), thereby inadvertently decoupling trocar (210), is reduced. Continued inward urging of trocar (210) further directs obturator tip (264) and cannula tip (24) distally through the layers of fat (4) and fascia (5) and into cavity (1), as shown in FIG. 8B.

Next, as shown in FIG. 8C, the clinician may pull obturator (216) proximally relative to cannula assembly (12) in order to decouple obturator (216) from cannula (12). In some instance, the clinician may hold cannula assembly (12) with one hand, while pulling obturator (216) with the other in order to overcome the friction fitting while keeping cannula assembly (12) suitably stationary within the abdominal cavity (1) of the patient. In other instances, the clinician may not have to hold cannula assembly (12) with one hand, such that the clinician may decuple obturator (216) from cannula assembly (12) by just pulling obturator (216).

The clinician may proximally actuate obturator (216) relative to cannula assembly (12) with sufficient force in order to overcome the frictional fitting between slanted upper surface (37) and tapered shaft surface (280). Additionally, the clinician may proximally actuate obturator (216) relative to cannula assembly (12) in order to overcome the frictional fitting between spring slips (272) and the surfaces of seal housing (30) defining slots (35). In instances where central portion (276) extends distally within slots (35) far enough to no longer make contact with portions of seal housing (30) defining slots (35), the clinician may proximally actuate obturator (216) relative to cannula assembly (12) with enough force to deform central portion (276) in order for central portion (276) to proximally actuate out of slots (35). After exemplary use, a user may suitably sterilize obturator (216) for another use.

Since spring clips (272) are configured to flex in response to longitudinal motion between cannula assembly (12) and obturator (216), the clinician is no longer required to provide a sufficient depression force (e.g. a pinching motion) to decouple obturator (216) from cannula assembly (12). Therefore, spring clips (272) may have an aspect ratio that includes a smaller length to thickness compared to latch arms (162). Additionally, spring clips (272) may be formed of a more robust material compared to latch arms (162) described above. Due to the smaller length to thickness ratio and the more robust material, spring clips (272) may be less vulnerable to damage during the sterilization process and/or in response to accidental contact.

Additionally, since spring clips (272) no longer require lateral motion in response to a sufficient depression force applied to buttons on domed upped body (266), base plate (268) requires no reinforcement slots and domed upper body (266) requires no apertures. Therefore, base plate (268) may be a solid plate such that the interior defined by base plate (268) and domed upper body (266) may be sealed from exterior fluid and matter. The lack of slots and apertures may help prevent outside fluid and other matter from entering into the interior of obturator head (260), which may in turn make it easier to clean and sterilize obturator (216) compared to obturator (116) described above.

In the current example, the proximal end of both legs (274) are fixed to the distal surface of base plate (268). However, in some instances, only one leg (274) may be fixed to the distal surface of base plate (268). While in the current example, central portion (276) forms a semi-cylindrical shape, any suitable shape may be used as would be apparent to one skilled in the art in view of the teachings herein. In the current example, legs (274) terminate into central portion (276) such that legs (274) are not coupled to each other. However, this is merely optional, as legs (274) may taper toward, and directly couple with each other such that central portion (276) is omitted entirely. In the current example, legs (274) are formed of a substantially planar surface. However, this is merely option, as surfaces of legs (274) may have any suitable geometry as would be apparent to one skilled in the art in view of the teachings herein, such as an undulating surface.

While in the current example obturator (216) is used in conjunction with cannula assembly (12) to form trocar (210), it should be understood that obturator (216) may be configured to be used with cannula assembly (112) described above such that friction coupling assembly (270) suitably mates with seal assembly (130) described above.

Figure 9:
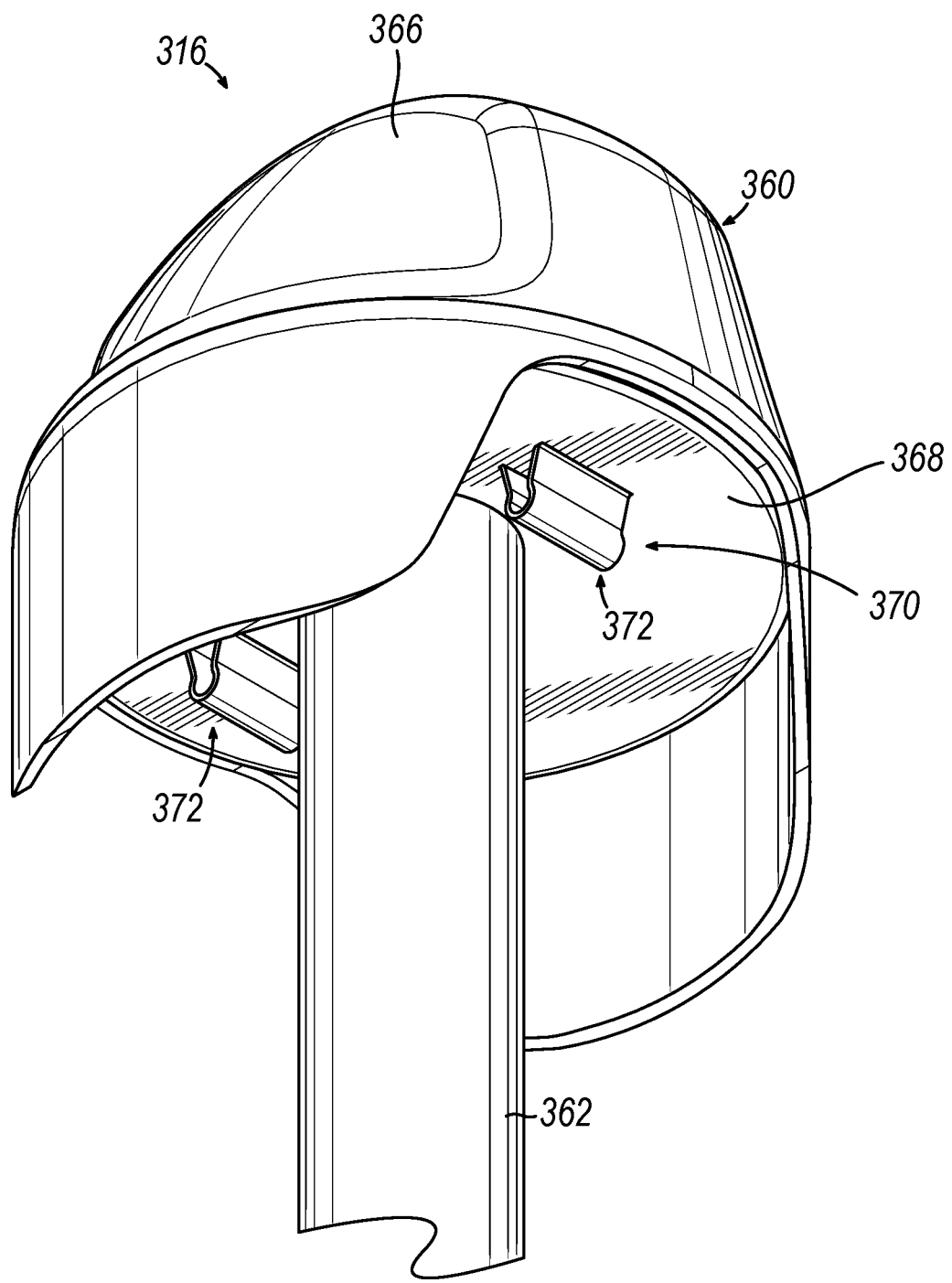
FIG. 9 depicts an enlarged perspective view of a proximal end of another exemplary obturator.

FIG. 9 shows another exemplary obturator (316) that may be used in replacement of obturator (216) described above. Obturator (316) is substantially similar to obturator (216) described above, with differences elaborated below. Obturator (316) includes a proximal head (360), an elongate cylindrical shaft (362) extending distally from proximal head (360), and a tapered distal tip (not shown); which are substantially similar to proximal head (260), elongate cylindrical shaft (262), and tapered distal tip (264) described above.

Obturator head (360) includes a domed upper body (366), a base plate (368), and a interference fit coupling assembly (370), which are substantially similar to domed upper body (266), base plate (268), and interference fit coupling assembly (270) described above, except interference fitting coupling assembly (370) only includes spring clips (372) and does not include a tapered shaft surface similar to surface (280) of obturator (216). Spring clips (372) are substantially similar to spring clips (272) described above. Therefore, spring clips (372) are dimensioned to fit within respective slots (35) of seal housing (30) in order to promote the coupling of obturator (316) with cannula assembly (12) via friction fitting.

Figure 10:
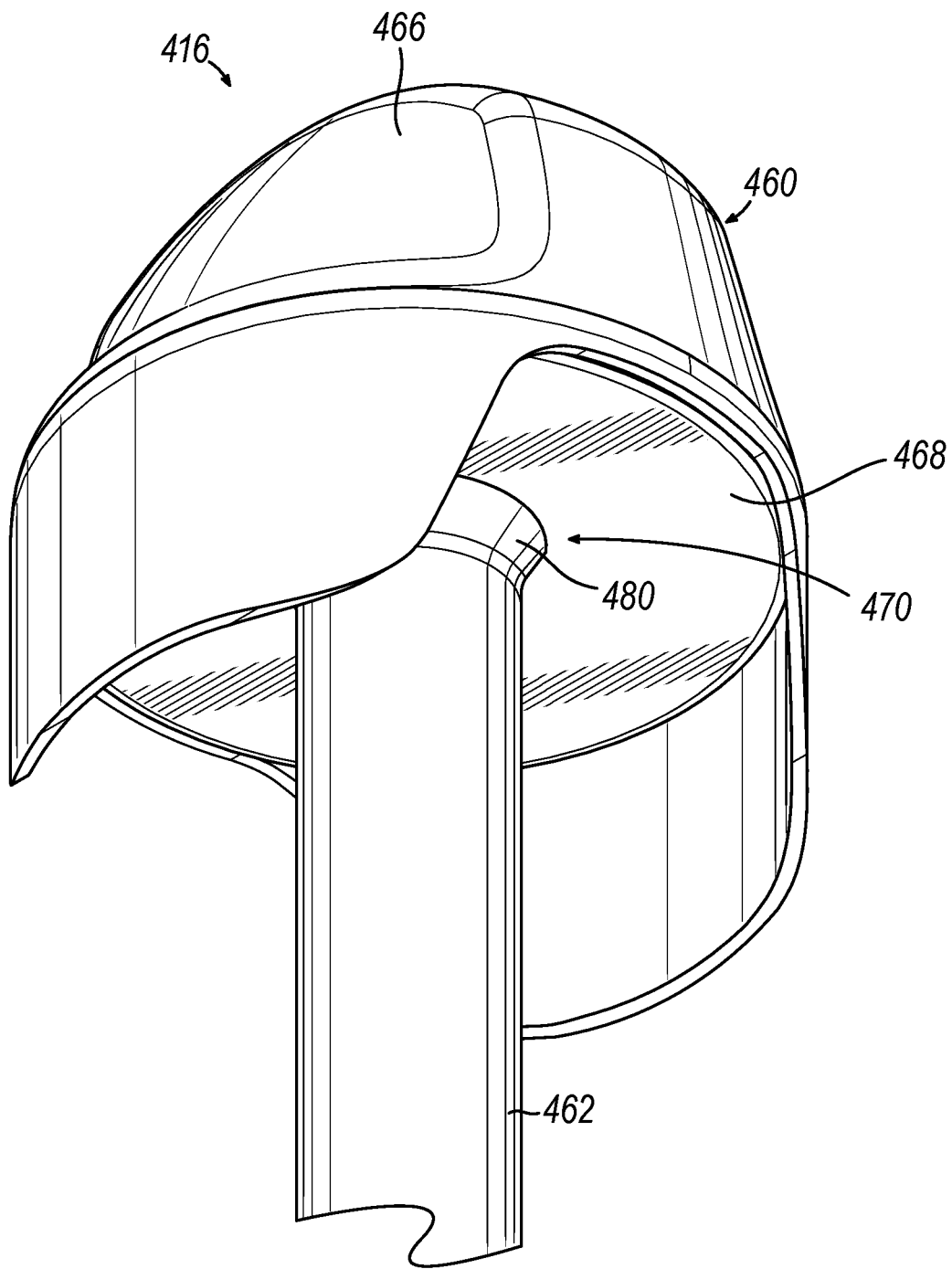
FIG. 10 depicts an enlarged perspective view of a proximal end of another exemplary obturator.

FIG. 10 shows another exemplary obturator (416) that may be used in replacement of obturator (216) described above. Obturator (416) is substantially similar to obturator (216) described above, with differences elaborated below. Obturator (416) includes a proximal head (460), an elongate cylindrical shaft (462) extending distally from proximal head (460), and a tapered distal tip (not shown); which are substantially similar to proximal head (260), elongate cylindrical shaft (262), and tapered distal tip (264) described above.

Obturator head (460) includes a domed upper body (466), a base plate (468), and an interference fit coupling assembly (470), which are substantially similar to domed upper body (266), base plate (268), and interference fit coupling assembly (270) described above, except interference fitting coupling assembly (470) only includes tapered shaft surface (480) and does not include spring clips similar to spring clips (272, 372) of obturators (216, 316). Tapered shaft surface (480) is substantially similar to tapered shaft surface (280) described above. Therefore, tapered shaft surface (480) is dimensioned to abut against a slanted upper surface (37) of seal housing (30) defining working channel (14) in order to promote the coupling of obturator (416) with cannula assembly (12) via friction fitting.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical access device comprising: (a) a cannula assembly including: (i) a cannula, (ii) a cannula head coupled with a proximal end of the cannula, and (iii) a working channel at least partially defined by the cannula and the cannula head extending longitudinally along a central axis of the cannula assembly, wherein the working channel is configured to receive a surgical instrument therethrough to access to a surgical site within a body cavity of a patient; and (b) an obturator, wherein the obturator is configured to removably couple with the cannula assembly along the central axis to facilitate insertion of the surgical access device through a body wall of the patient, wherein the obturator comprises: (i) an elongated shaft extending along a longitudinal axis, wherein the elongated shaft is dimensioned to fit within the working channel of the cannula assembly, (ii) a tapered distal tip located at a distal portion of the elongated shaft, and (iii) an obturator head located at a proximal portion of the elongated shaft, wherein the obturator head comprises an interference fit feature configured to inhibit proximal movement between the obturator and the cannula assembly via a frictional force against a surface of the cannula assembly.

Example 2

The surgical access device of Example 1, wherein the obturator head comprises a base plate and a domed body, wherein the base plate and the domed body define an interior area.

Example 3

The surgical access device of Example 2, wherein the base plate and the domed body form a seal around the interior area.

Example 4

The surgical access device of any one or more of Examples 2 through 3, wherein the interference fit feature extends distally from the base plate.

Example 5

The surgical access device of Example 4, wherein the interference fit feature comprises a tapered surface extending from the shaft assembly to the base plate.

Example 6

The surgical access device of any one or more of Examples 4 though 5, wherein the cannula head comprises a seal assembly comprising a slanted upper surface defining a portion of the working channel.

Example 7

The surgical access device of Example 6, wherein the tapered surface is configured to engage the slanted upper surface to generate at least a portion of the friction force.

Example 8

The surgical access device of any one or more of Examples 2 through 7, wherein the interference fit feature comprises a downwardly extending pin coupled to the base plate.

Example 9

The surgical access device of Example 8, wherein the canula head comprises a seal assembly defining a slot located adjacent to the working channel, wherein the downwardly extending pin is configured to engage a portion of the seal assembly defining the slot to generate at least a portion of the friction force.

Example 10

The surgical access device of Example 9, wherein the downwardly extending pin comprises a spring clip formed from a resilient material.

Example 11

The surgical access device of Example 10, wherein the spring clip comprises a pair of legs attached to the base plate.

Example 12

The surgical access device of Example 11, wherein the spring clip further comprises a central body attached to a distal end of each leg in the pair of legs.

Example 13

The surgical access device of Example 12, wherein the central body comprises a semi-tubular shape.

Example 14

The surgical access device of Example 13, wherein the spring clip and the base plate together define an open-ended pathway.

Example 15

The surgical access device of any one or more of Examples 1 through 14, wherein the obturator is formed of a surgical steel.

Example 16

The surgical access device of any one or more of Examples 1 through 15, wherein the interference fit feature is attached to the elongated shaft.

Example 17

The surgical access device of any one or more of Examples 1 through 16, wherein the interference fit feature is spaced away from the elongated shaft.

Example 18

A surgical access device comprising: (a) a cannula assembly including: (i) a cannula, (ii) a cannula head coupled with a proximal end of the cannula, wherein the cannula head comprises a first engagement surface, and (iii) a working channel at least partially defined by the cannula and the cannula head extending longitudinally along a central axis of the cannula assembly, wherein the working channel is configured to receive a surgical instrument therethrough to access to a surgical site within a body cavity of a patient; and (b) an obturator, wherein the obturator is configured to removably couple with the cannula assembly along the central axis to facilitate insertion of the surgical access device through a body wall of the patient, wherein the obturator comprises: (i) an elongated shaft extending along a longitudinal axis, wherein the elongated shaft is dimensioned to fit within the working channel of the cannula assembly, (ii) a tapered distal tip located at a distal portion of the elongated shaft, and (iii) an obturator head located at a proximal portion of the elongated shaft, wherein the obturator head comprises an interference fit feature comprising a second engagement surface configured to abut against the first engagement surface to generate a frictional force while the obturator is coupled with the cannular assembly, wherein the interference fit feature is configured to inhibit proximal translation of the obturator relative to the cannula assembly.

Example 19

The surgical access device of Example 18, wherein the second engagement surface is attached to the elongated shaft.

Example 20

A surgical access device comprising: (a) a cannula assembly including: (i) a cannula, (ii) a cannula head coupled with a proximal end of the cannula, and (iii) a working channel at least partially defined by the cannula and the cannula head extending longitudinally along a central axis of the cannula assembly, wherein the working channel is configured to receive a surgical instrument therethrough to access to a surgical site within a body cavity of a patient; and (b) an obturator, wherein the obturator is configured to removably couple with the cannula assembly along the central axis to facilitate insertion of the surgical access device through a body wall of the patient, wherein the obturator comprises: (i) an elongated shaft extending along a longitudinal axis, wherein the elongated shaft is dimensioned to fit within the working channel of the cannula assembly, (ii) a tapered distal tip located at a distal portion of the elongated shaft, and (iii) an obturator head located at a proximal portion of the elongated shaft, wherein the obturator head is configured to engage the cannula head while the obturator is coupled with the cannula assembly, wherein the obturator head comprises an interference fit feature configured to deform itself or a portion of the cannula head in order to inhibit proximal translation of the obturator relative to the cannula head via frictional engagement.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338281 on Nov. 4, 2021; U.S. patent application Ser. No. 17/213,401, entitled "Pinch-To-Clamp Cannula Depth Limiter," filed on even date herewith Mar. 26, 2021, published as U.S. Pub. No. 2021/0338273 on Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 on Nov. 4, 2021; U.S. patent application Ser. No. 17/213,416, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021, issued as U.S. Pat. No. 11,712,267 on Aug. 1, 2023; U.S. patent application Ser. No. 17/213,431, entitled "Two Piece Separable Obturator," filed on even-date-herewith Mar. 26, 2021, published as U.S. Pub. No. 2021/0338275 on Nov. 4, 2021; U.S. patent application Ser. No. 17/213,437, entitled "Balancing Feature for Reusable Trocar," filed on Mar. 26, 2021, issued as U.S. Pat. No. 11,559,329 on Jan. 24, 2023; U.S. patent application Ser. No. 17/213,508, entitled "Airflow Channels and Patterns in Lumen for Cannula," filed on Mar. 26, 2021, published as U.S. Pub. No. 2021/0338278 on Nov. 4, 2021; and/or U.S. patent application Ser. No. 17/213,508, entitled "Stabilizer for Surgical Shafts or Cannulas," filed on Mar. 26, 2021, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical access device comprising:
(a) a cannula assembly including:
 (i) a cannula,
 (ii) a cannula head coupled with a proximal end of the cannula, wherein the cannula head comprises a seal assembly defining a slot, and
 (iii) a working channel at least partially defined by the cannula and the cannula head extending longitudinally along a central axis of the cannula assembly, wherein the working channel is configured to receive a surgical instrument therethrough to access to a surgical site within a body cavity of a patient, wherein the slot defined by the seal assembly is located adjacent to the working channel; and
(b) an obturator, wherein the obturator is configured to removably couple with the cannula assembly along the central axis to facilitate insertion of the surgical access device through a body wall of the patient, wherein the obturator comprises:
- (i) an elongated shaft extending along a longitudinal axis, wherein the elongated shaft is dimensioned to fit within the working channel of the cannula assembly,
- (ii) a tapered distal tip located at a distal portion of the elongated shaft, and
- (iii) an obturator head located at a proximal portion of the elongated shaft, wherein the obturator head comprises a base plate, wherein the obturator head comprises an interference fit feature configured to inhibit proximal movement between the obturator and the cannula assembly via a frictional force against a surface of the cannula assembly, wherein the interference fit feature comprises a downwardly extending pin coupled to the base plate, wherein the downwardly extending pin is configured to engage a portion of the seal assembly defining the slot to generate at least a portion of the friction force, wherein the downwardly extending pin comprises a spring clip formed from a resilient material, wherein the spring clip comprises a pair of legs, wherein each leg of the pair of legs is attached to the base plate.

2. The surgical access device of claim 1, wherein the obturator head comprises a domed body, wherein the base plate and the domed body define an interior area.

3. The surgical access device of claim 2, wherein the base plate and the domed body form a seal around the interior area.

4. The surgical access device of claim 2, wherein the interference fit feature extends distally from the base plate.

5. The surgical access device of claim 1, wherein the spring clip further comprises a central body attached to a distal end of each leg in the pair of legs.

6. The surgical access device of claim 5, wherein the central body comprises a semi-tubular shape.

7. The surgical access device of claim 6, wherein the spring clip and the base plate together define an open-ended pathway.

8. The surgical access device of claim 1, wherein the obturator is formed of a surgical steel.

9. The surgical access device of claim 1, wherein the interference fit feature is attached to the elongated shaft.

10. The surgical access device of claim 1, wherein the interference fit feature is spaced away from the elongated shaft.

11. A surgical access device comprising:
(a) a cannula assembly including:
- (i) a cannula,
- (ii) a cannula head coupled with a proximal end of the cannula, wherein the cannula head comprises a first engagement surface, and
- (iii) a working channel at least partially defined by the cannula and the cannula head extending longitudinally along a central axis of the cannula assembly, wherein the working channel is configured to receive a surgical instrument therethrough to access to a surgical site within a body cavity of a patient, wherein the first engagement surface of the cannula head defines a slot located adjacent to the working channel; and
(b) an obturator, wherein the obturator is configured to removably couple with the cannula assembly along the central axis to facilitate insertion of the surgical access device through a body wall of the patient, wherein the obturator comprises:
- (i) an elongated shaft extending along a longitudinal axis, wherein the elongated shaft is dimensioned to fit within the working channel of the cannula assembly,
- (ii) a tapered distal tip located at a distal portion of the elongated shaft, and
- (iii) an obturator head comprising a base plate, wherein the obturator head is located at a proximal portion of the elongated shaft, wherein the obturator head comprises an interference fit feature comprising a resilient spring clip comprising a first resilient leg and a second resilient leg extending distally from the base plate, wherein the first resilient leg and the second resilient leg each terminate into a distal head such that the distal head couples the first resilient leg and the second resilient leg, wherein the first resilient leg and the second resilient leg are configured to deform towards each other in response to simultaneously engaging the first engagement surface to generate a frictional force while the obturator is coupled with the cannula assembly, wherein the first engagement surface and both the first resilient leg and the second resilient leg are configured to inhibit proximal translation of the obturator relative to the cannula assembly, wherein the obturator is configured to decouple from the cannula assembly in response to manually pulling the obturator head proximally along the longitudinal axis.

12. The surgical access device of claim 11, wherein the interference fit feature further comprises a second engagement surface, wherein the second engagement surface is attached to the elongated shaft, wherein the second engagement surface is configured to engage a portion defining the working channel.

13. A surgical access device comprising:
(a) a cannula assembly including:
- (i) a cannula,
- (ii) a cannula head coupled with a proximal end of the cannula, wherein the cannula head comprises a seal assembly defining a slot, and
- (iii) a working channel at least partially defined by the cannula and the cannula head extending longitudinally along a central axis of the cannula assembly, wherein the working channel is configured to receive a surgical instrument therethrough to access to a surgical site within a body cavity of a patient, wherein the slot defined by the seal assembly is located adjacent to the working channel; and
(b) an obturator, wherein the obturator is configured to removably couple with the cannula assembly along the central axis to facilitate insertion of the surgical access device through a body wall of the patient, wherein the obturator comprises:
- (i) an elongated shaft extending along a longitudinal axis, wherein the elongated shaft is dimensioned to fit within the working channel of the cannula assembly,
- (ii) a tapered distal tip located at a distal portion of the elongated shaft, and
- (iii) an obturator head located at a proximal portion of the elongated shaft, wherein the obturator head is configured to engage the cannula head while the obturator is coupled with the cannula assembly, wherein the obturator head comprises:

(A) a dome,
(B) a base plate,
(C) an interference fit feature comprising a first resilient leg and a second resilient leg, wherein the first resilient leg and the second resilient leg are attached directly to the base plate, wherein the first resilient leg and the second resilient leg are configured to engage a portion of the seal assembly defining the slot to inhibit proximal translation of the obturator relative to the cannula head via frictional engagement.

* * * * *